(12) United States Patent
Okada et al.

(10) Patent No.: US 6,799,696 B2
(45) Date of Patent: Oct. 5, 2004

(54) DELIVERY APPARATUS FOR PARTS

(75) Inventors: Noriyoshi Okada, Shizuoka Pref. (JP); Sadahiro Watanabe, Shizuoka Pref. (JP)

(73) Assignee: Olympus Corporation, Tokyo (JP)

( * ) Notice: Subject to any disclaimer, the term of this patent is extended or adjusted under 35 U.S.C. 154(b) by 37 days.

(21) Appl. No.: 10/241,188

(22) Filed: Sep. 11, 2002

(65) Prior Publication Data

US 2003/0047418 A1 Mar. 13, 2003

(30) Foreign Application Priority Data

Sep. 12, 2001 (JP) ........................................ 2001-276272

(51) Int. Cl.$^7$ ................................................ B65H 3/60
(52) U.S. Cl. ........................ 221/200; 221/202; 221/254
(58) Field of Search .................................. 221/254, 158, 221/159, 160, 163, 165, 172, 202, 200, 236, 239, 258

(56) References Cited

U.S. PATENT DOCUMENTS

| | | | | |
|---|---|---|---|---|
| 3,447,707 A | * | 6/1969 | Furst ........................... 414/414 |
| 3,567,006 A | * | 3/1971 | Bell et al. ..................... 198/396 |
| 4,735,343 A | * | 4/1988 | Herzog ......................... 221/159 |
| 5,318,200 A | * | 6/1994 | Allen et al. .................... 221/192 |
| 5,702,030 A | * | 12/1997 | Hulscher ....................... 221/254 |
| 6,227,407 B1 | * | 5/2001 | Simeri et al. ................... 221/254 |
| 6,371,330 B1 | * | 4/2002 | Knez ............................ 221/200 |

* cited by examiner

Primary Examiner—David H. Bollinger
(74) Attorney, Agent, or Firm—Scully, Scott Murphy & Presser (57) ABSTRACT

An apparatus for delivering parts such as pipette chips in succession to an intended position includes a transfer section. The transfer section includes a stepped portion for changing a transfer passage to upper and lower passages to provide a difference in height between the upper and lower passages, which is in more than a size of the parts. The transfer section further includes a separator for holding on the upper passage an upper part of at least two parts being transferred in overlapping relationship one on the other and causing the lower part of the two parts to drop by gravity onto the lower passage and continuously thereto causing the upper part itself to drop onto the lower passage. A recovery duct is preferably provided upstream of the transfer section. With the above construction, no overlapping parts are delivered to a part supply section and no waste parts occur due to a trouble in transferring.

4 Claims, 8 Drawing Sheets

DELIVERY APPARATUS FOR PARTS

BACKGROUND OF THE INVENTION

The present invention relates to an apparatus suitable for delivering parts as pipette tips used in dispensing reagents or liquids to be inspected or other similar operations to intended positions for chemicobiological analysis, immunity analysis and the like, which is intended to realize effective delivery of such parts by preventing troubles in transfer due to overlapping of the parts.

In the field of the chemicobiological or immunity analysis, pipettes (dispensing nozzles) are used for dispensing liquids to be inspected and the like. In order to avoid unintentional contamination of the pipette in dispensation, a disposable tip is fitted at the distal end of the pipette, which is to be replaced with new one in every dispensation.

In usual, there is a need for previously preparing parts of this kind in bulk to perform continuous dispensing operations, so that they are generally received and stored in a hopper. To the effective replacement of these parts, moreover, it is inevitable to arrange them taken out of the hopper rapidly and regularly so as to permit these parts to be transferred to intended positions.

A hitherto used apparatus for delivering parts taken out of a hopper in regularly aligned state includes a conveyor for taking the parts one by one from the hopper where the parts are accumulated, and a transfer section for causing the parts taken by the conveyor to fall from its upper end into a gripping space so as to permit the parts to be hung in upright positions, thereby transferring the parts in alignment with one another in a row. Such an apparatus has been disclosed in Japanese Patent Application Opened No. 2000-19182, in which pipette tips are aligned and taken out of a hopper so as to be supplied to tip racks automatically.

Figure 8:
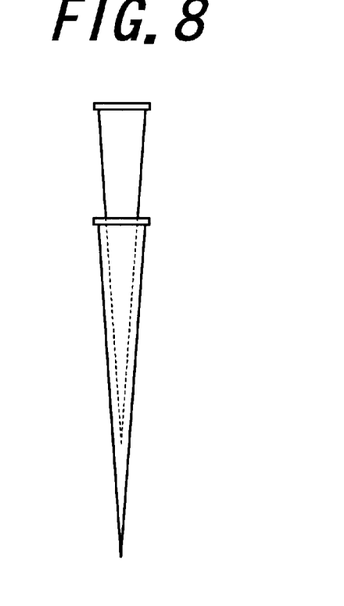
FIG. 8 is a view illustrating an overlapping state of two parts to be delivered.

With such a delivery apparatus, however, parts tend to overlap one upon the other as shown in FIG. 8, because the parts are accumulated in a random fashion in a hopper, and this tendency is particularly acute in tapered shaped pipette tips. When the overlapping pipette tips have arrived at the transfer section, the parts would interfere with components of the apparatus and tend to bind on the transfer passage to cause an impediment to intended dispensation.

Figure 9:
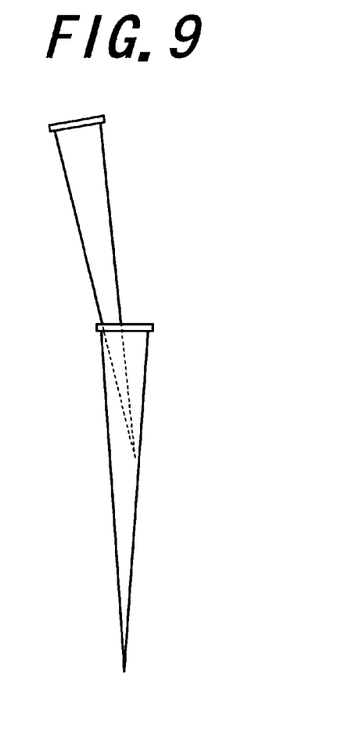
FIG. 9 is a view illustrating another overlapping state of two parts.

In order to eliminate such a trouble, an attempt has been made to provide interfering members acting upon upper parts of the overlapping parts. Even with this precaution, the interfering members insufficiently operates with the overlapping parts, so that upper parts are often positioned obliquely relative to the lower parts as shown in FIG. 9 and delivered in this state to intended positions. Even if the overlapping relation of the parts is eliminated, the upper parts would tumble down from the transfer section, so that waste or useless parts occur. These are unsolved problems.

SUMMARY OF THE INVENTION

It is an object of the invention to provide an apparatus for delivering parts, which eliminates any overlapping parts to be delivered without any occurrence of waste parts, and thus, overcomes all the disadvantages of the prior art.

In order to accomplish the above object, the apparatus according to the invention for delivering parts such as pipette tips in succession includes a transfer section comprising a stepped portions for changing a transfer passage to upper and lower passages to provide a difference in height between said upper and lower passages, which is more than a size of said parts, and a separator for holding on said upper passage an upper part of at least two parts being transferred in overlapping relationship one on the other and causing the lower part of said two parts to drop by gravity onto said lower passage and continuously thereto causing said upper part itself to drop onto said lower passage.

In the apparatus constructed described above, it is particularly preferable that the separator comprises a passage extending in parallel with said transfer passage of the transfer section so as to grip only the upper part in upright hung state, and an opening located at the forward end of the passage of the separator for dropping said upper part therethrough.

Preferably, the stepped portion has an inclined passage gradually connecting the upper and lower passages.

According to a preferred embodiment of the invention, there is provided a recovery duct for returning parts removed in the transfer section to a hopper upstream of the transfer section, to prevent any occurrence of waste parts.

According to the invention it is possible to eliminate the overlapping of parts to deliver them one by one in alignment with one another, thereby preventing any stoppage of operating line due to overlapping of parts. The parts dislodged from the delivery line are restored to the hopper so that they can be supplied again by the conveyor to the transfer section without any occurrence of waste parts.

The invention will be more fully understood by referring to the following detailed specification and claims taken in connection with the appended drawings.

DESCRIPTION OF THE PREFERRED EMBODIMENTS

Figure 1:
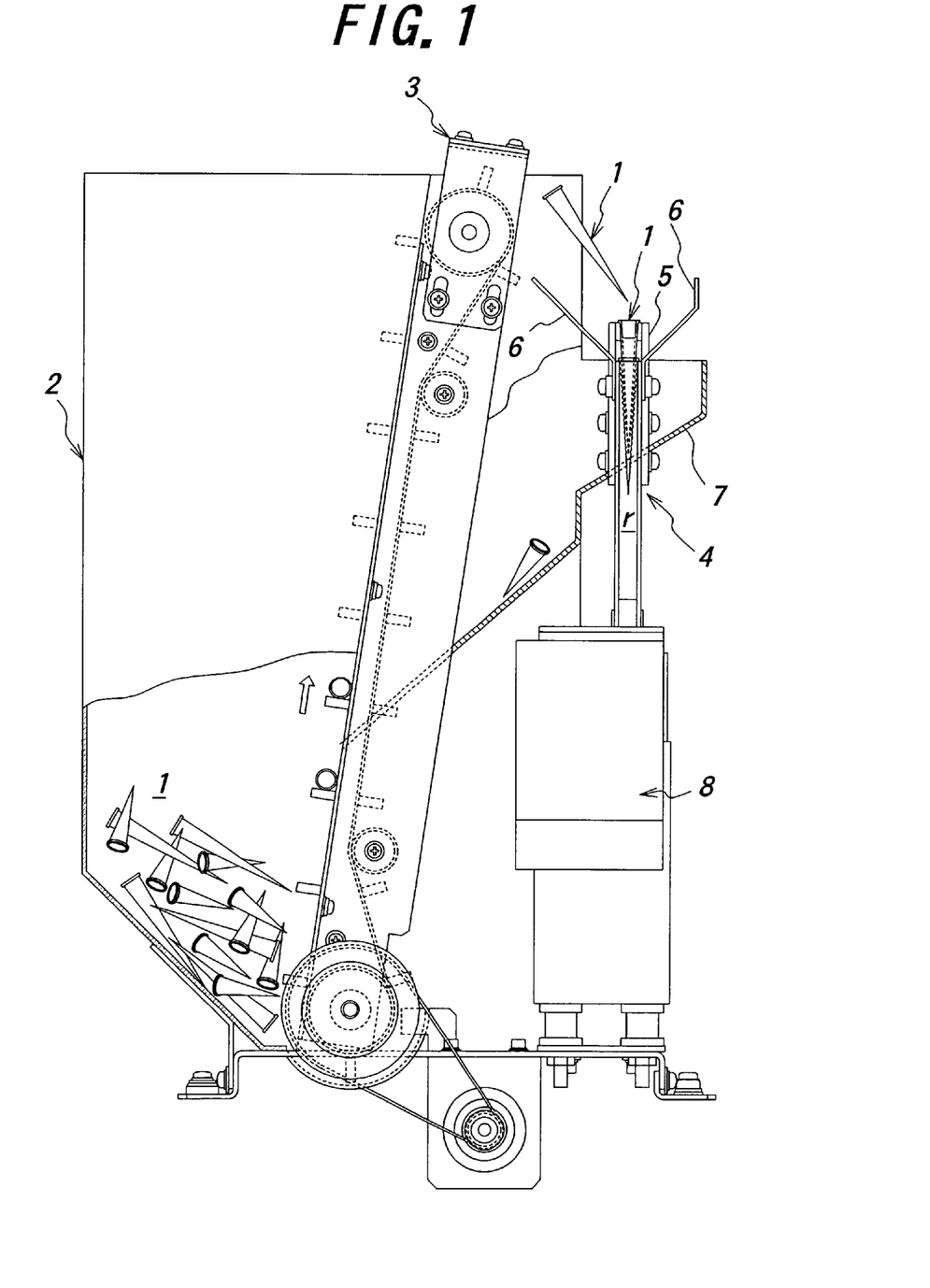
FIG. 1 is a side view illustrating the delivery apparatus for parts according to the invention.
Figure 2:
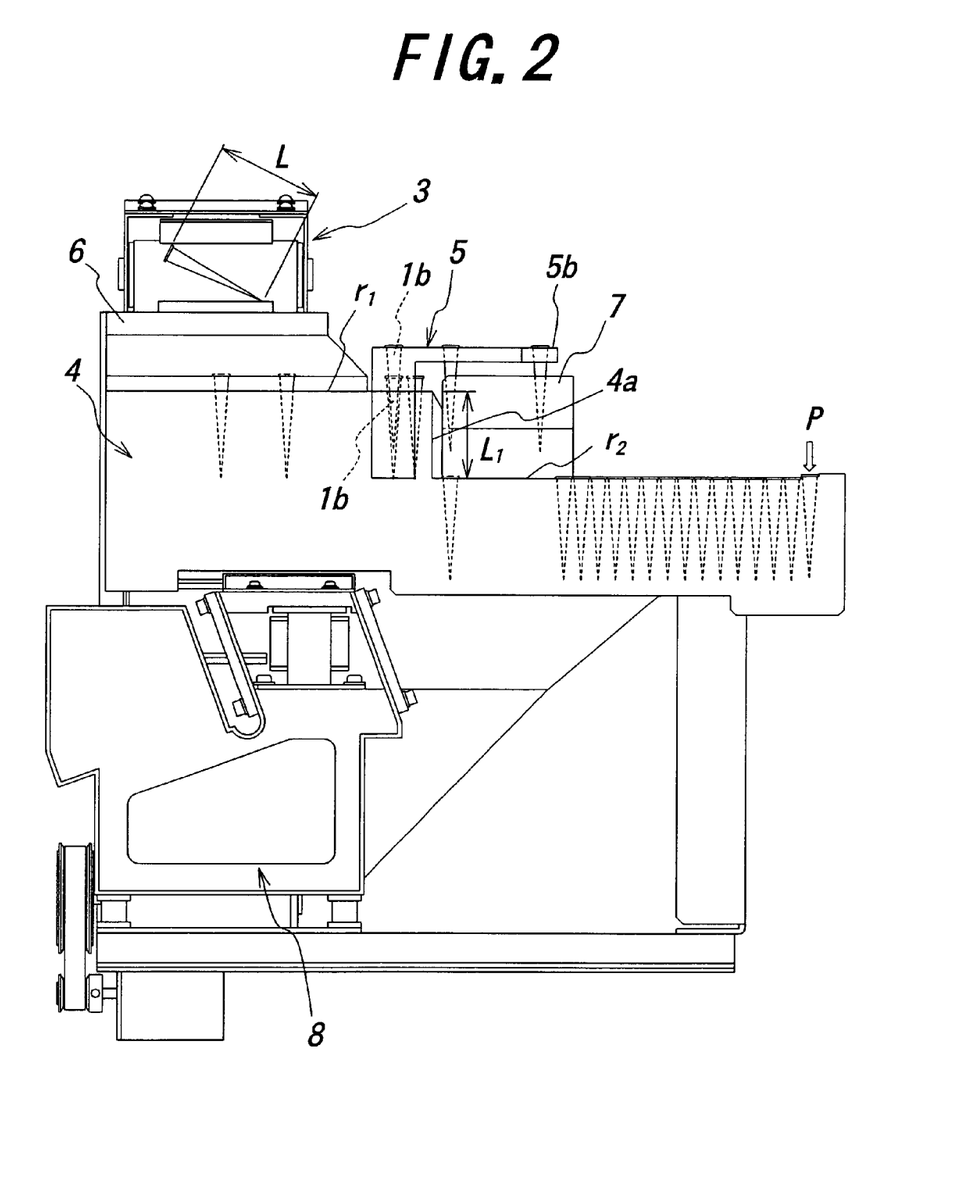
FIG. 2 is a front elevation of the apparatus shown in FIG. 1.

The present invention will be concretely explained in more detail by referring to the drawings hereinafter. FIGS. 1 and 2 illustrate a delivery apparatus for parts according to the invention in side and front views, respectively.

In FIGS. 1 and 2, the apparatus comprises a hopper 2 for accumulating therein a great number of parts 1, such as pipette tips, a bucket conveyor 3 for scooping up the parts 1 accumulated in the hopper 2 one by one to cause them to drop from its upper end, and a transfer section 4 where the parts 1 dropped from the upper end of the bucket conveyor 3 are gripped on both sides to permit the parts to be hung upright. In the transfer section 4, in this manner, the parts 1 kept upright are then aligned at least in a row and fed in succession along a transfer passage r to a next section.

Figure 3:
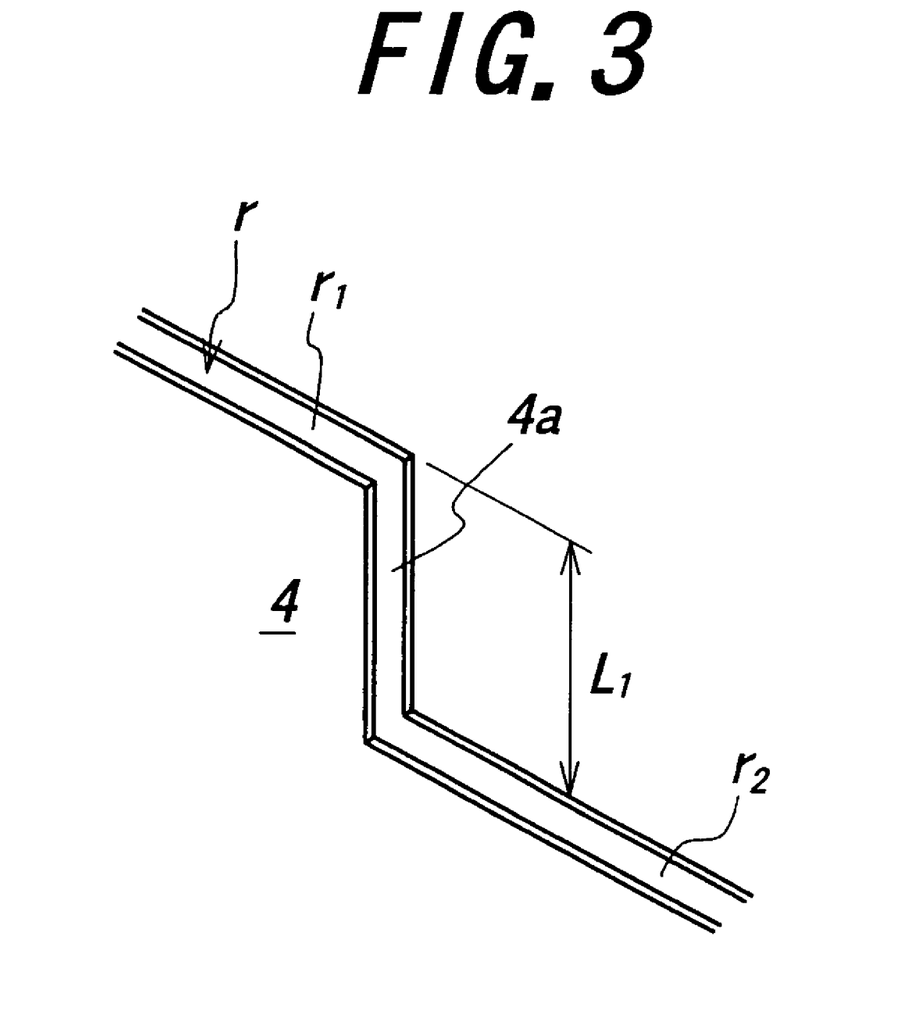
FIG. 3 is a view showing an important part of the apparatus shown in FIG. 1 on a large scale.

The transfer section 4 comprises at least two plates which are adapted to be vibrated in vertical directions to transfer along the transfer passage r the parts 1 on the passage r in the horizontal direction. On its way, there is provided a stepped portion 4a dividing the transfer passage r into upper and lower passages $r_1$ and $r_2$ as shown on an enlarged scale in FIG. 3. The height $L_1$ of the stepped portion 4a or the difference in height between the upper and lower passages $r_1$ and $r_2$ is more than the length L of the parts 1.

Figure 4:
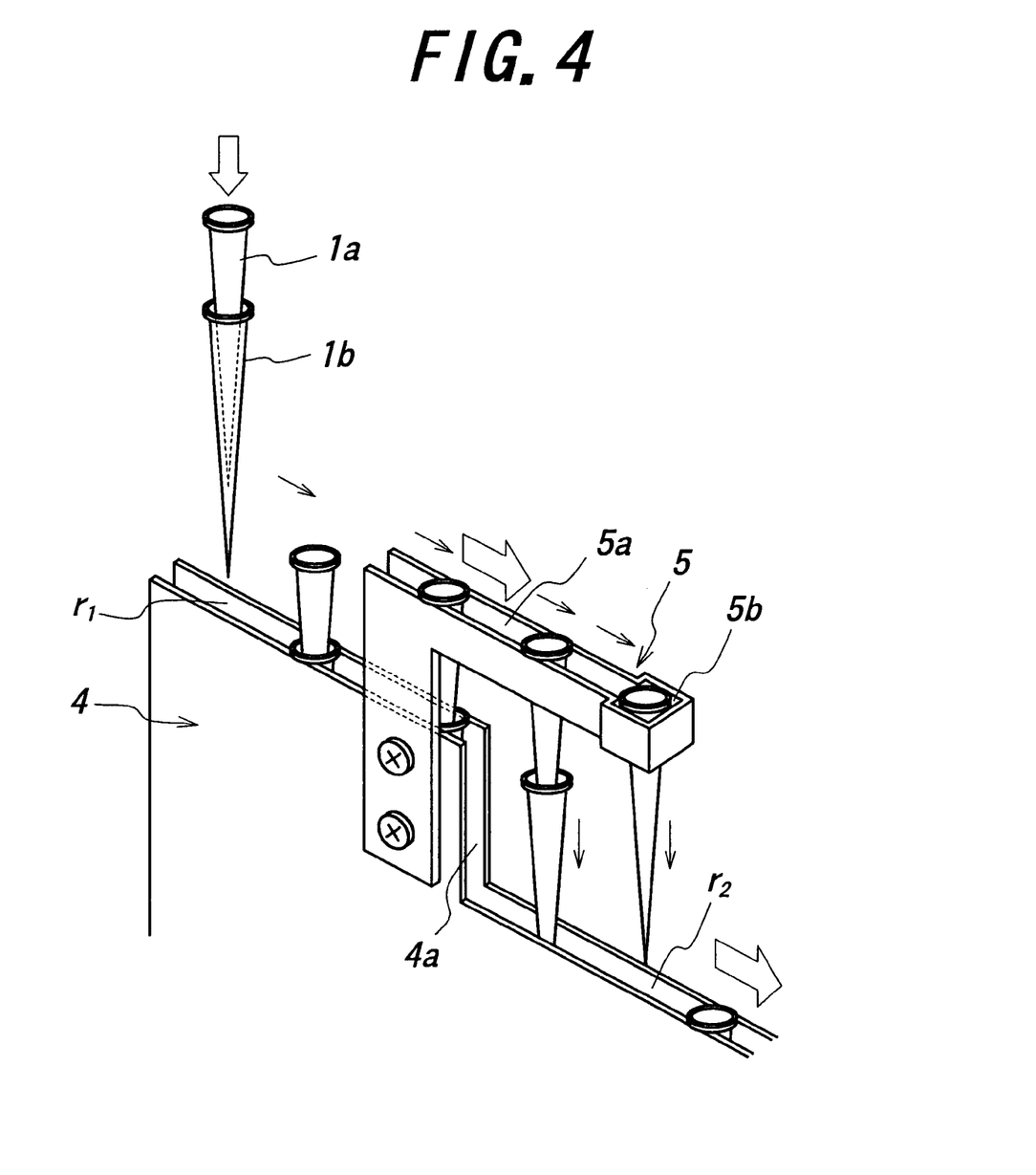
FIG. 4 is a perspective view of the outline of the separator used in the apparatus shown in FIG. 1.

With reference again to FIGS. 1 and 2, there is shown a separator 5 fixed and held by plates forming the upper passage $r_1$ of the transfer section 4 as shown in the perspective view of FIG. 4. The separator 5 comprises a passage 5a extending in parallel with the transfer passage r and, when two overlapping parts are being transferred, holding the upper part 1a thereof, and an opening portion 5b located at the forward end of the passage 5a for dropping therethrough the upper part 1a onto the lower passage $r_2$. The upper part 1a on the upper passage $r_1$ is moved toward the opening portion 5b with the aid of the vibration of the transfer section 4. On the other hand, the lower part 1b separated from the upper part 1a falls at the stepped portion 4a by gravity onto the lower passage $r_2$.

Returning to FIGS. 1 and 2, the apparatus further comprises a guide 6 for guiding the parts 1 dropped from the conveyor 2 to the transfer section 4, a recovery duct 7 for restoring the upper parts 1a removed at the transfer section 4 to the hopper 2, and vibration plates 8 for vibrating the plates of the transfer section 4.

With the above arrangement of the apparatus, the parts 1 in the hopper 2 are scooped up by the bucket conveyor 3 so as to be dropped from its upper end so that the parts are gripped in hang positions by the plates of the transfer section 4 and aligned with one another in a row in the hung positions. In this manner, the aligned parts 1 are successively delivered through the upper and lower passages $r_1$ and $r_2$ to a supply section p for the parts.

In more detail, when two parts scooped up by the bucket conveyor 3 are supplied in overlapping state one upon the other into transfer passage r, the upper part 1a meets the passage 5a of the separator 5 and is supported by the passage 5a so as to proceed thereon. On its way, at the stepped portion 4a, the lower part 1b falls by gravity onto the lower passage $r_2$. On the other hand, when the upper part 1a arrives at the opening portion 5b of the separator 5, the upper part 1a falls through the opening portion 5b onto the lower passage $r_2$, so that the upper and lower parts 1a and 1b are aligned in a row on the lower passage $r_2$ so as to deliver one by one to the supply section p, even if they are supplied in the overlapping state to the transfer passage r.

Figure 5:
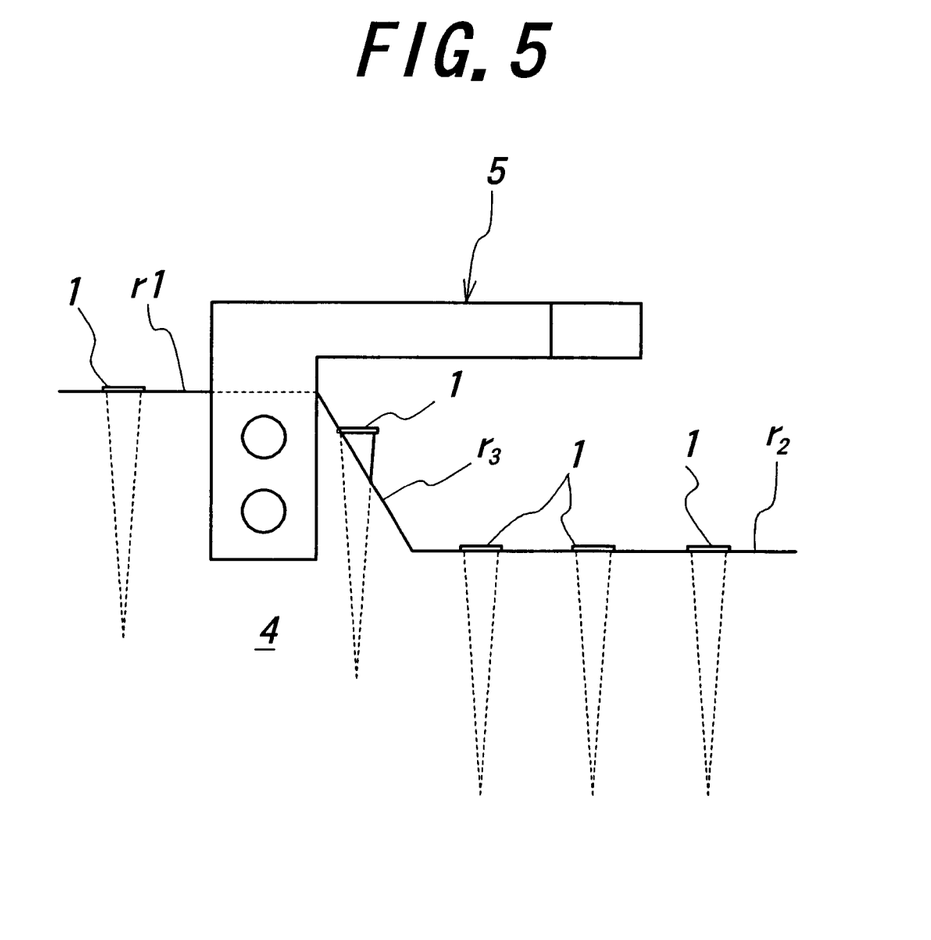
FIG. 5 illustrates a modification of part of the apparatus according to the invention.

While the stepped portion 4a is exemplarily shown in vertically connecting the upper and lower passages $r_1$ and $r_2$ in FIGS. 1 and 2, it will be apparent that it may be an inclined stepped portion $r_3$ for obtaining a smooth transition from the upper passage $r_1$ to the lower passage $r_2$ as shown in FIG. 5.

Figure 6:
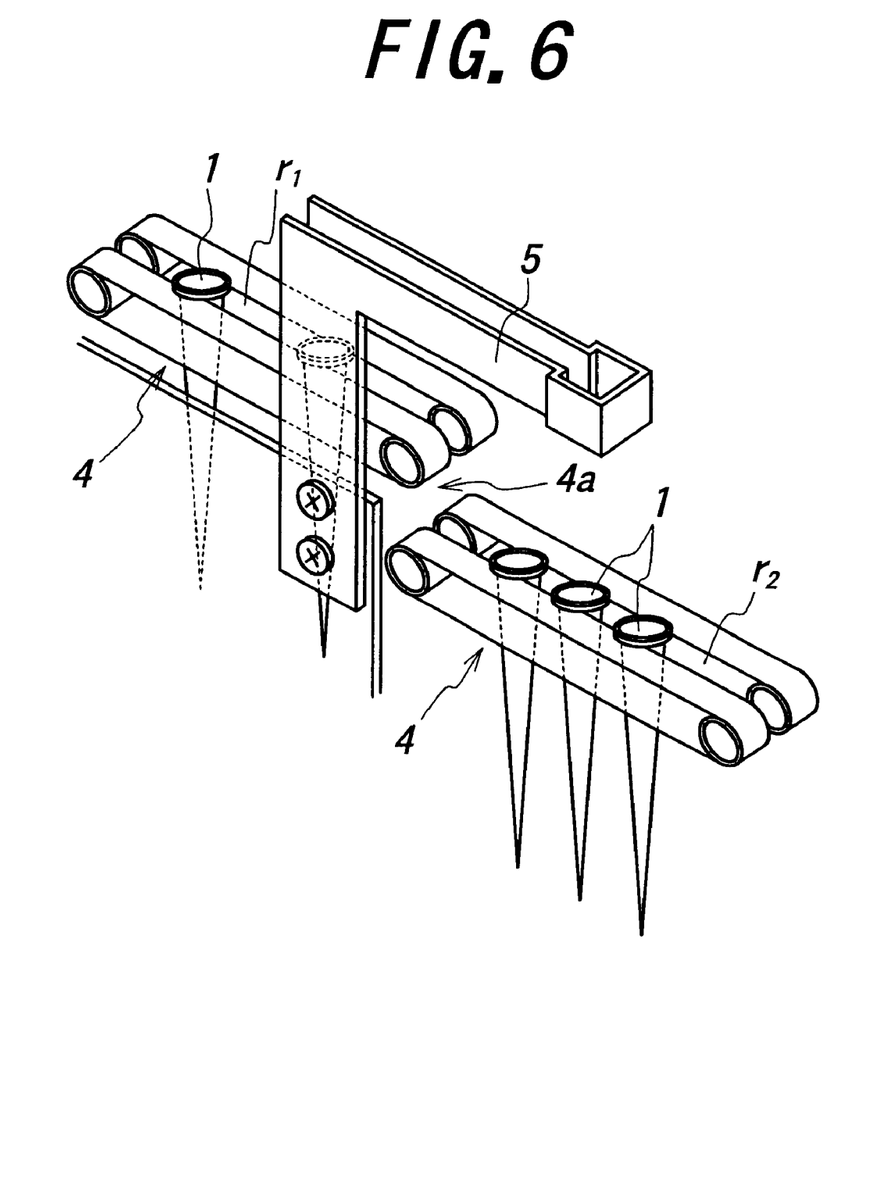
FIG. 6 illustrates a modification of another part of the apparatus according to the invention.

Although the transfer section 4 provided with the vibration plates shown in the above embodiment, it is to be understood that belt-pulleys may be used as driving means as shown in FIG. 6. The present invention should not be limited, however, to the specific features of the transfer section 4. As described above, however, the height $L_1$ of the stepped portion 4a or the difference in height between the upper and lower passages $r_1$ and $r_2$ is preferably more than the length L of the parts 1 to ensure that when two parts proceeding on the transfer passage r are in overlapping relationship, the lower part 1b is caused to be dropped onto the lower passage $r_2$. In the case of employing the belt-pulleys for the driving means in the transfer section 4, the separator 5 may be constructed to use the driving means utilizing the vibration for transferring the parts 1 (1b) on the passage 5a similarly to that shown in FIGS. 1 and 2. However, the separator 5 may employ belt-pulley driving means (not shown) in the similar manner to the transfer section 4.

The hopper 2 for accumulating the parts therein may be a box type or a ball type. In order to return parts to the hopper 2 when they are removed from the transfer section 4 without proceeding on the transfer passage r, a recovery duct 7 connected to the hopper 2 is preferably provided in the proximity of the stepped portion 4a.

Figure 7:
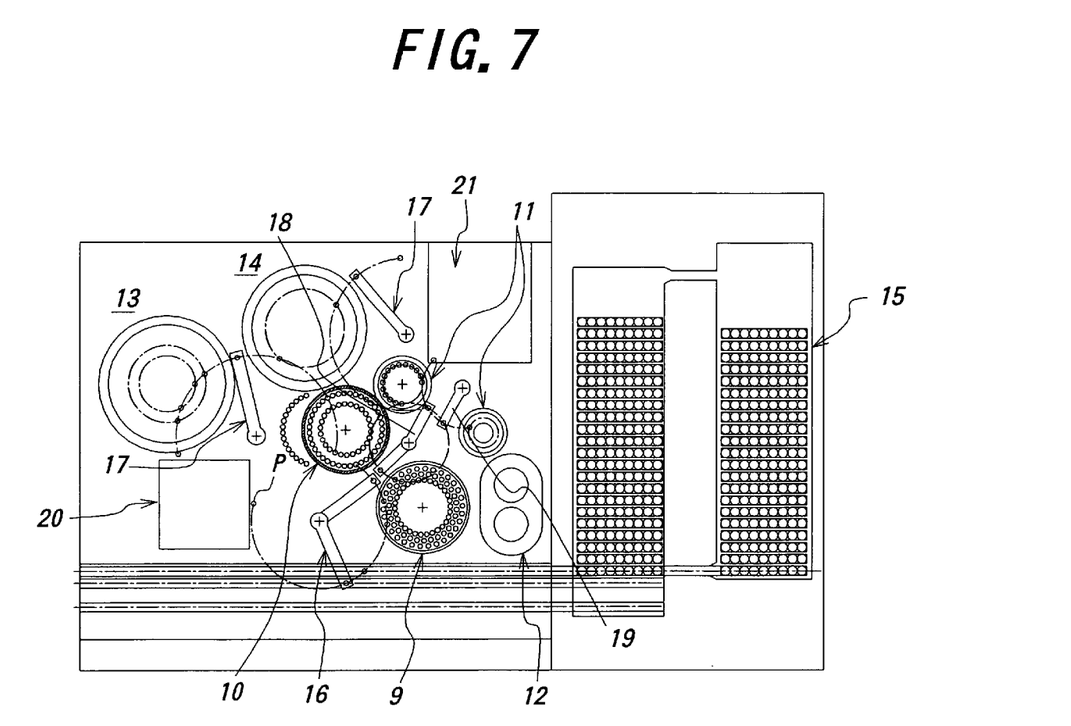
FIG. 7 is a plan view of an entire construction of an automatic analyzing apparatus to which the apparatus according to the invention is applicable.

FIG. 7 illustrates in a plan view an automatic analyzing apparatus suitable for use in immunity analysis, showing its entire construction. The apparatus shown in FIG. 7 comprises a reaction table 9, a stirrer or agitator 10, a detecting reaction table 11, a vessel 12 for containing a substrate liquid, vessels 13 and 14 for containing reagents, a sampler 15 having a rack receiving portion for receiving sample racks and a rack transfer portion for transferring the racks in the rack receiving portion in succession to sample dispensing positions, and a sample dispensing nozzle 16 for collecting samples from racks supplied by the sampler 15 to dispensing them to required reaction vessels or reactors.

In FIG. 7 the apparatus further comprises a reagent dispensing nozzle 17 for sampling the reagents from reagent bottle arranged in the reagent vessels 13 and 14, transfer portions 18 and 19 for suitably transferring the reaction vessels to respective tables, a pipette tip supply unit 20 for supplying pipette tips to be fitted on distal ends of the sample dispensing nozzles 15, and a reaction vessel supply unit 21.

The delivery apparatus for parts according to the present invention is applicable to the pipette tip supply unit 20 shown in FIG. 7. The delivery apparatus for parts according to the invention can deliver tips aligned in a row successively to a tip supply section p where rods of sample dispensing nozzles 16 are fitted in pipette tips, thereby enabling to dispense samples or reagents with satisfactory efficiency.

While the invention has been particularly shown and described with reference to preferred embodiments thereof, it will be understood by those skilled in the art that the foregoing and other changes in form and details can be made therein without departing from the spirit and scope of the invention.

What is claimed is:

1. An apparatus for delivering parts such as pipette tips in succession and including a transfer section, said transfer section comprising a stepped portion for changing a transfer passage to upper and lower passages to provide a difference in height between said upper and lower passages, which is more than a size of said parts, and a separator for holding on said upper passage an upper part of at least two parts being transferred in overlapping relationship one on the other and causing the lower part of said two parts to drop by gravity onto said lower passage and continuously thereto causing said upper part itself to drop onto said lower passage.

2. The apparatus for delivering parts as set forth in claim 1, wherein said separator comprises a passage extending in parallel with said transfer passage of said transfer section for gripping only the upper part to hold it in upright hung state, and an opening located at the forward end of said passage of the separator for dropping said upper part therethrough.

3. The apparatus for delivering parts as set forth in claim 1, wherein said stepped portion has an inclined passage gradually connecting said upper and lower passages.

4. The apparatus for delivering parts as set forth in claim 1, wherein said apparatus further comprises a recovery duct for returning parts removed in said transfer section to a hopper upstream of said transfer section.

* * * * *